(12) United States Patent
Kahn (10) Patent No.: US 12,268,807 B1
(45) Date of Patent: Apr. 8, 2025

(54) DEVICES, SYSTEMS, AND METHODS FOR PROVIDING INDIVIDUALIZED DELIVERY OF SUSPENDED MEDICATION

(71) Applicant: YALE UNIVERSITY, New Haven, CT (US)

(72) Inventor: Peter Kahn, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 18/389,897

(22) Filed: Dec. 20, 2023

(51) Int. Cl.
*A61M 15/00* (2006.01)

(52) U.S. Cl.
CPC .... *A61M 15/0086* (2013.01); *A61M 15/0013* (2014.02); *A61M 15/0021* (2014.02)

(58) Field of Classification Search
CPC .......... A61M 15/0816; A61M 15/0833; A61M 15/0858; A61M 15/0086–0088; A61M 15/0013; A61M 15/0021; A61M 11/00; A61M 11/02; A61M 2205/52
See application file for complete search history.

(56) References Cited

U.S. PATENT DOCUMENTS

| | | | |
|---|---|---|---|
| 4,945,929 A * | 8/1990 | Egilmex | A61M 11/002 131/273 |
| 4,984,158 A * | 1/1991 | Hillsman | A61M 15/009 600/536 |
| 2003/0178022 A1 | 9/2003 | Davies et al. | |
| 2003/0205226 A1 | 11/2003 | Gallem et al. | |
| 2011/0155129 A1 | 6/2011 | Stedman et al. | |
| 2012/0085344 A1 * | 4/2012 | Luber | A61M 15/0085 128/203.29 |
| 2012/0145150 A1 | 6/2012 | Donovan et al. | |
| 2017/0333645 A1 * | 11/2017 | Alizoti | A61B 5/087 |
| 2018/0133417 A1 | 5/2018 | Krishna et al. | |
| 2018/0200459 A1 | 7/2018 | Rowland et al. | |
| 2018/0272084 A1 * | 9/2018 | Reiner | A61M 15/0065 |
| 2019/0328039 A1 | 10/2019 | Romming et al. | |
| 2023/0149375 A1 | 5/2023 | Surber | |
| 2023/0201514 A1 * | 6/2023 | Zapol | A61M 16/1005 128/202.26 |

OTHER PUBLICATIONS

Vincken et al., Spacer devices for inhaled therapy: why use them, and how? ERJ Open Res 2018; 4: 00065-2018 [https://doi.org/10.1183/23120541.00065-2018] pp. 1-10.

(Continued)

*Primary Examiner* — Elliot S Ruddie
(74) *Attorney, Agent, or Firm* — Barclay Damon LLP; Anthony P. Gangemi (57) ABSTRACT

A medication delivery assistance device includes a chamber housing that defines an interior space. A first input port is at a first end of the chamber housing, an output port is at a second end of the chamber housing, and a second input port is in the chamber housing. The first input port is configured to receive a portion of an inhaler that is configured to deliver medication into the interior space. The output port has a user interface that is configured to define a medication flow path from the first input port through the interior space and out the output port. The second input port is configured to receive at least a portion of an external fluid source that is configured to deliver a fluid into the interior space to accelerate movement of the medication along the medication flow path.

20 Claims, 5 Drawing Sheets

(56) References Cited

OTHER PUBLICATIONS

McIvor et al., Optimizing the Delivery of Inhaled Medication for Respiratory Patients: The Role of Valved Holding Chambers, Hindawi, Canadian Respiratory Journal vol. 2018, Article ID 5076259, 8 pages https://doi.org/10.1155/2018/5076259.
Nikander, et al. The Evolution of Spacers and Valved Holding Chambers, Journal of Aerosol Medicine and Pulmonary Drug Delivery, vol. 27, Supplement 1, 2014, Mary Ann Liebert, Inc. pp. S-4-S-23 DOI: 10.1089/jamp.2013.1076.
Mitchell, et al. Valved holding chambers (VHCs) for use with pressurised metered-dose inhalers (pMDIs): a review of causes of inconsistent medication delivery, Primary Care Respiratory Journal (2007); 16(4): 207-214.
Boulet, et al. Canadian asthma consensus report, 1999, Supplement to CMAJ 1999; 161(11 Suppl) S1-S62.

* cited by examiner

DEVICES, SYSTEMS, AND METHODS FOR PROVIDING INDIVIDUALIZED DELIVERY OF SUSPENDED MEDICATION

FIELD

The present technology relates generally to the field of pulmonary medicine delivery, and more particularly, to medication delivery assistance devices and systems and methods for providing individualized delivery of suspended medication.

BACKGROUND

Currently, a large number of medications used in the field of pulmonary medicine are delivered via the inhalational route. The use of inhalation facilitates the direct delivery of an active pharmaceutical compound to the end organ of interest (i.e., the lungs), thus maximizing on-target effects for a given dose of medication and minimizing off-target effects. Additionally, inhalation can provide a convenient method to deliver medication without requiring access to swallowing, intravenous, or subcutaneous methods of administration. Definitionally, the use of inhaled medications requires the need for appropriate delivery mechanisms. These delivery mechanisms can introduce uncertainty and human factors deviations from suggested desired use protocols. Unlike pills, liquid, or other forms of medications which are simply swallowed or injected after which time the active pharmaceutical ingredient ("API") becomes available for therapeutic activity, inhaled therapeutics rely on the patient to inhale the API correctly using both appropriate technique and quantity of the delivered medication for this medication to have its desired effect and minimize off target or undesired effects.

To date, there have been two main modalities of drug delivery for inhalational use: the nebulizer and inhaler. While the nebulizer is an appealing way to deliver medication as it requires only passive tidal breathing on the part of the patient, nebulized medications take significantly longer time to deliver, may expose the user and surrounding personnel to the API, may result in imprecise dosing of medication, and is not able to accommodate all types of APIs as some may not be able to be formulated or are not available for nebulization. Additionally, not all nebulizers are portable, and they require careful cleaning after use. Unlike nebulizers, inhalers deliver a known quantity of medication in each actuation, are portable, can deliver combination therapies and can do so in a time efficient manner.

Unfortunately, given that the inhaler is a medical device, its proper use is not always guaranteed, thus impacting the delivery of the desired therapeutic. A higher number of inhaler use errors have been shown to lead to worse outcomes for chronic obstructive pulmonary disease ("COPD") as well as asthma patients. The most significant complication most frequently encountered in the world of pulmonary medicine is the lack of a patient's ability to readily understand and appropriately deploy the inhaler with consistent technique. This is exacerbated by the multiple different types of inhalers marketed, many of which require different techniques to correctly deliver the API. Although a medication may be most appropriate for a patient, therapeutic benefit may not be achieved due to human factors challenges, most prominently the lack of a patient's ability to coordinate their inhalation with the simultaneous deployment of an actuation from an inhaler.

As a result of these challenges healthcare providers have worked to design inhaler teaching programs to ensure that patients are properly educated on how to deploy respiratory medications via an inhaler both during the initial phase of use and in maintenance phases thereafter. Medication delivery assistance devices such as spacers and valved holding chambers have been developed in an effort to deliver medication when patients are unable to synchronously breathe in with the deployment of an inhaler. Other solutions include the use of placebo inhalers to propose appropriately timed inhalation, audio-based teaching devices, digital videos, and other teaching-based modalities to support patient learning.

While these solutions are helpful for some patients, not all medications can be used with a spacer and not all patients are able to effectively coordinate their inhalation with all inhaler types even with repeated prompting or teaching. For example, the reduction in deposition of large particles in the oropharynx is often perceived by patients as a reduction in drug delivery and leads to patient noncompliance with the device. Additionally, not all inhaler types can be used by all patient types due to mismatches in patient abilities to generate appropriate flow for each inhaler or the lack of a medication being prepared in the desired formulation. As a result, valved holding chambers have been developed to assist patients in deploying an inhaler. Valved holding chambers provide improved coordination of inhalation, reduced deposition in the oropharynx, real-time feedback on inhalation, reduced exacerbations, delayed time to exacerbation occurrence, and reduced cost of exacerbations if they occur. While valved holding chambers can provide a bridge for some patients, not all patients are able to inhale with sufficient force or in coordination with their valved holding chamber to sufficiently deliver their medication.

What is needed, therefore, are improved medication delivery assistance devices and systems and methods for coaching the use of inhalers with medication delivery assistance devices that address at least some of the problems described above.

SUMMARY

According to an embodiment of the present technology, a medication delivery assistance device is provided. The medication delivery assistance devices includes a chamber housing that defines an interior space. A first input port is at a first end of the chamber housing, an output port is at a second end of the chamber housing, and a second input port is in the chamber housing. The first input port is configured to receive a portion of an inhaler that is configured to deliver medication into the interior space. The output port has a user interface that is configured to define a medication flow path from the first input port through the interior space and out the output port. The second input port is configured to receive at least a portion of an external fluid source that is configured to deliver a fluid into the interior space to accelerate movement of the medication along the medication flow path.

In some embodiments, the output port includes a valve in the user interface. The valve is moveable between a closed position and an open position such that the output port defines the medication flow path when the valve is in the open position.

In some embodiments, the external fluid source is a fan, a compressed gas tank, a pump, oscillating membranes, a chemical reactor, a user chargeable bladder or canister having a handheld bellows mechanism, chemical reactions, fans, pistons, or other electronic mechanisms, etc.

In some embodiments, the fluid includes ambient air, oxygen, hydrogen, argon, helium, nitrogen, chlorofluorocarbon, hydroflouroalkanes, hydrofluoroolefin, any other suitable propellant, or combinations thereof.

In some embodiments, the external fluid source is configured to deliver the fluid into the interior space synchronously with the valve being moved to the open position.

In some embodiments, the external fluid source is configured to deliver the fluid into the interior space at a predetermined interval after the valve is moved to the open position.

In some embodiments, the external fluid source is configured to deliver the fluid into the interior space at a predetermined interval before the valve is moved to the open position.

In some embodiments, the external fluid source is configured to deliver the fluid into the interior space synchronously with a user engaging the user interface.

In some embodiments, the external fluid source is configured to deliver the fluid into the interior space at a predetermined interval after a user engages the user interface.

In some embodiments, the external fluid source is configured to deliver the fluid into the interior space at a predetermined interval before a user engages the user interface.

According to another embodiment of the present technology, an individualized medication delivery system is provided. The system includes a medication delivery assistance device that includes a chamber housing defining an interior space, a first input port at a first end of the chamber housing, a second input port in the chamber housing, and an output port at a second end of the chamber housing. The output port has a user interface that is configured to define a medication flow path from the first input port through the interior space and out the output port. An inhaler is partially received in the first input port and is configured to deliver medication into the interior space of the chamber housing. An external fluid source is at least partially received in the second input port and is configured to deliver a fluid into the interior space to accelerate movement of the medication along the medication flow path. A sensor is configured to obtain respiratory behavior data of a user of the system. A computing device is configured to receive the respiratory behavior data. The computing device includes inhaler coaching circuitry and a memory configured to execute instructions of the inhaler coaching circuitry via at least one processor. The instructions include steps for obtaining, via the sensor, respiratory behavior data of the user; receiving, at the computing device, the respiratory behavior data; performing a respiratory pattern analysis algorithm on the respiratory behavior data to determine a desired interval of medication delivery; communicating a first cue signal to actuate the inhaler to deliver the medication into the interior space of the chamber housing; communicating a second cue signal to actuate the external fluid source; and communicating a third cue signal to the user to inhale to achieve the desired interval of medication delivery.

In some embodiments, the instructions further include obtaining, via the sensor, medication delivery data based on the user's inhalation in response to the third cue signal; receiving, at the computing device, the medication delivery data; performing a medication delivery analysis algorithm on the medication delivery data to assess the efficacy of the medication delivery; and adjusting, if the efficacy of the medication delivery is below a predetermined threshold, at least one of the first, second, and third cue signals to improve the efficacy of a future medication delivery.

In some embodiments, performing the respiratory pattern analysis algorithm includes analyzing the respiratory behavior data to determine a current breathing pattern of the user; confirming that the current breathing pattern is predictable within a predetermined margin of error; confirming that the current breathing pattern is compatible with medication delivery via the inhaler and the valved holding chamber; and synchronizing the current breathing pattern with the actuation of the external fluid source to determine the desired interval of medication delivery.

In some embodiments, performing the medication delivery analysis algorithm includes determining if the user inhaled at the desired interval; creating medication delivery instance data log based, at least in part, on the medication delivery data; communicating the medication delivery instance data log to a database; correlating the medication delivery instance data log with historical data of the user and historical data of similarly diagnosed third party users stored on the database to track and monitor symptoms, side-effects, and exacerbations of a pathological condition of the user being treated by the medication; determining the efficacy of the medication delivery based, at least in part, on the correlated medication delivery instance data log; and developing an adjusted cue signal to improve the efficacy of a future medication delivery.

In some embodiments, the first and second cue signals are communicated to the user and/or the user's healthcare provider, and the first, second, and third cue signals each include an audio cue, a visual cue, a haptic cue, or combinations thereof.

According to yet another embodiment of the present technology, a method of coaching a user on medication delivery via an inhaler and a medication delivery assistance device is provided. The method includes providing a medication delivery assistance device that includes a chamber housing defining an interior space, a first input port at a first end of the chamber housing, a second input port in the chamber housing, and an output port at a second end of the chamber housing, the output port having a user interface configured to define a medication flow path from the first input port through the interior space and out the output port; providing an inhaler partially received in the first input port and configured to deliver medication into the interior space of the chamber housing; providing an external fluid source at least partially received in the second input port and configured to deliver a fluid into the interior space to accelerate movement of the medication along the medication flow path; obtaining, via a sensor, respiratory behavior data of the user; receiving, at a computing device, the respiratory behavior data; performing a respiratory pattern analysis algorithm on the respiratory behavior data to determine a desired interval of medication delivery; communicating a first cue signal to actuate the inhaler to deliver the medication into the interior space of the chamber housing; communicating a second cue signal to actuate the external fluid source; and communicating a third cue signal to the user to inhale to achieve the desired interval of medication delivery.

In some embodiments, the method further includes obtaining, via the sensor, medication delivery data based on the user's inhalation in response to the third cue signal; receiving, at the computing device, the medication delivery data; performing a medication delivery analysis algorithm on the medication delivery data to assess the efficacy of the medication delivery; and adjusting, if the efficacy of the medication delivery is below a predetermined threshold, at least one of the first, second, and third cue signals to improve the efficacy of a future medication delivery.

Further objects, aspects, features, and embodiments of the present technology will be apparent from the drawing Figures and below description.

BRIEF DESCRIPTION OF DRAWINGS

Some embodiments of the present technology are illustrated as an example and are not limited by the figures of the accompanying drawings, in which like references may indicate similar elements.

DETAILED DESCRIPTION

Figure 1A:
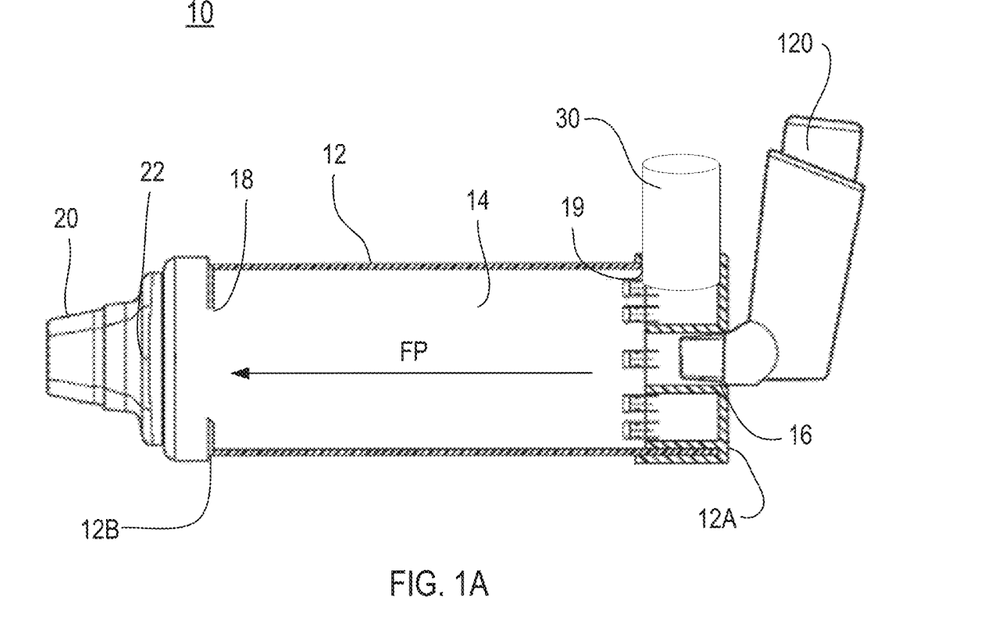
FIG. 1A is a partial cross-sectional view of a mediation delivery assistance device according to some embodiments of the present technology.

FIG. 1A illustrates a medication delivery assistance device 10 according to some embodiments of the present technology. Device 10 includes a chamber housing 12 that defines an interior space 14. A first input port 16 is at a first end 12A of the chamber 12. The first input port 16 is configured to receive a portion of an inhaler 120 that is configured to deliver medication into the interior space 14. In some embodiments, the inhaler 120 is a pressurized metered-dose inhaler. In other embodiments, the inhaler 120 is a soft mist inhaler.

An output port 18 is at a second end 12B of the chamber housing 12. The output port 18 includes a user interface 20, such as a mouthpiece, that is configured to define a medication flow path FP from the first input port 16 through the interior space 14 and out the output port 18. The user interface 20 that has a valve 22 therein such that the device 10 is a valved holding chamber. The valve 22 is moveable between a closed position and an open position based on a user interacting with the user interface 20. For example, when the user inhales through user interface 20 the valve is configured to move to the open position to allow contents within the chamber housing 12 to flow into the user's mouth and lungs, and when the exhales into the user interface 20 the valve is configured to move to the closed position to prevent the user's exhaled breath from entering the chamber housing 12. Thus, the user interface 20 defines the medication flow path FP from the first input port 16 through the interior space 14 and out the output port 18 when the valve 22 is in the open position.

The chamber housing 12 includes a second input port 19 therein. The second input port 19 is configured to receive at least a portion of an external fluid source 30 that is configured to deliver a fluid (i.e., a gas or a liquid) into the interior space 14 to accelerate movement of the medication along the medication flow path FP. In some embodiments, the external fluid source 30 is configured to deliver the fluid into the interior space 14 synchronously with the valve 22 being moved to the open position. In some embodiments, the external fluid source 30 is configured to deliver the fluid into the interior space 14 at a predetermined interval before the valve 22 is moved to the open position. In some embodiments, the external fluid source 30 is configured to deliver the fluid into the interior space 14 at a predetermined interval after the valve 22 is moved to the open position. The predetermined interval for actuating the external fluid source 30 is determined via algorithms of inhaler coaching circuitry of a computing device, as discussed in more detail below. In the embodiment shown in FIG. 1A, the second input port 19 is located in a side of the chamber housing 12 and is adjacent to the first end 12A. However, the present technology is not limited thereto and contemplates embodiments in which the second input port 19 is located at the first end 12A, at the second end 12B, or at any location along a side of the chamber housing 12 between the first end 12A and the second end 12B.

In some embodiments, the external fluid source 30 is a fan, a compressed gas tank, a pump (e.g., an electric pump, a pneumatic pump, a hydraulic pump, a manual pump, etc.), oscillating membranes, a chemical reactor (e.g., a device that utilizes chemical reactions to generate flow), a user chargeable bladder or canister having a handheld bellows mechanism, chemical reactions, fans, pistons, or other electronic mechanisms, or any other device or system configured to generate flow of the fluid into the interior space 14. In some embodiments, the fluid includes ambient air, oxygen, hydrogen, argon, helium, nitrogen, chlorofluorocarbon, hydroflouroalkanes, hydrofluoroolefin, any other suitable propellant, or combinations thereof. For example, in some embodiments the fluid includes ambient air enriched with some or all of the previously mentioned fluids in various mixtures.

In some embodiments, a flow regulator is associated with the fluid source 30 to manage the volume and/or speed of flow into the interior space 14. The particular design and implementation of a flow regulator varies by embodiment. For example, a flow regulator is employed in some embodiments that utilize compressed gas as the external fluid source.

Figure 1B:
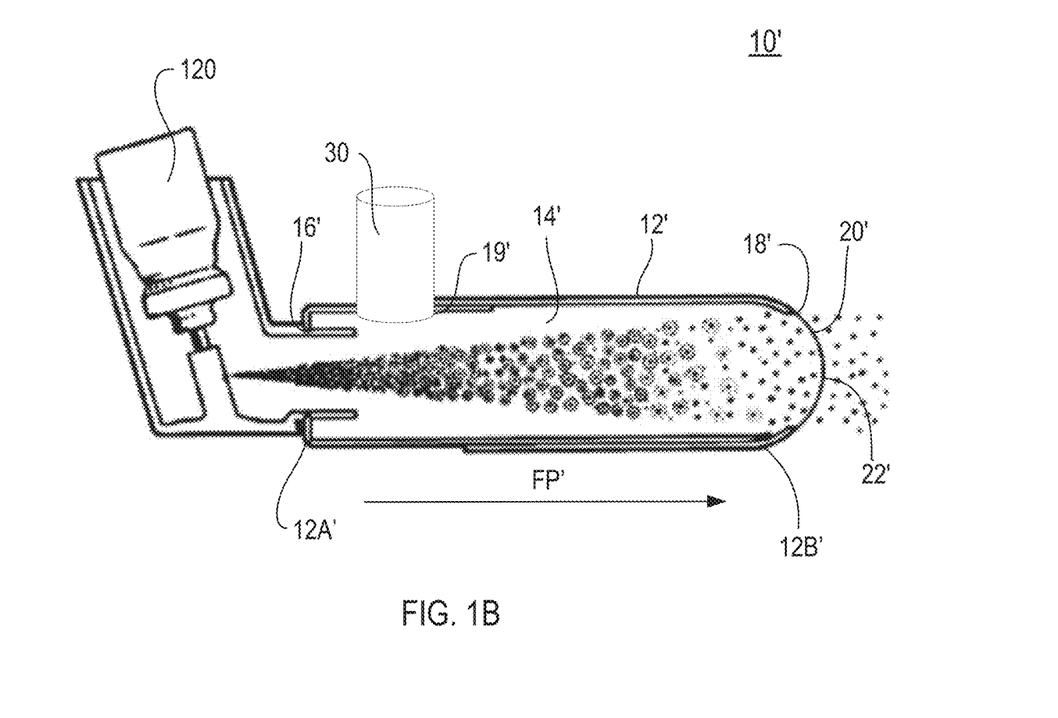
FIG. 1B is a partial cross-sectional view of a mediation delivery assistance device according to some embodiments of the present technology.

FIG. 1B illustrates a medication delivery assistance device 10' according to some embodiments of the present technology. Device 10' includes a chamber housing 12' that defines an interior space 14'. A first input port 16' is at a first end 12A' of the chamber 12'. The first input port 16' is configured to receive a portion of an inhaler 120 that is configured to deliver medication into the interior space 14'. In some embodiments, the inhaler 120 is a pressurized metered-dose inhaler. In other embodiments, the inhaler 120 is a soft mist inhaler.

An output port 18' is at a second end 12B' of the chamber housing 12'. The output port 18' includes a user interface 20', such as a mouthpiece, that is configured to define a medication flow path FP' from the first input port 16' through the interior space 14' and out the output port 18'. The user interface 20' is substantially hollow and has an open end 22' such that the device 10' is a spacer. Thus, the user interface 20' defines the medication flow path FP' from the first input port 16' through the interior space 14' and out the output port 18' via the open end 22' of the user interface 20'.

The chamber housing 12' includes a second input port 19' therein. The second input port 19' is configured to receive at least a portion of an external fluid source 30 that is configured to deliver a fluid (i.e., a gas or a liquid) into the interior space 14' to accelerate movement of the medication along the medication flow path FP'. In some embodiments, the external fluid source 30 is configured to deliver the fluid into the interior space 14' synchronously with a user engaging the user interface 20'. In some embodiments, the external fluid source 30 is configured to deliver the fluid into the interior space 14' at a predetermined interval before a user engages the user interface 20'. In some embodiments, the external fluid source 30 is configured to deliver the fluid into the interior space 14' at a predetermined interval after a user engages the user interface 20'. The predetermined interval for actuating the external fluid source 30 is determined via algorithms of inhaler coaching circuitry of a computing device, as discussed in more detail below. In the embodiment shown in FIG. 1B, the second input port 19' is located in a side of the chamber housing 12' and is adjacent to the first end 12A'. However, the present technology is not limited thereto and contemplates embodiments in which the second input port 19' is located at the first end 12A', at the second end 12B', or at any location along a side of the chamber housing 12' between the first end 12A' and the second end 12B'.

In some embodiments, the external fluid source 30 is a fan, a compressed gas tank, a pump (e.g., an electric pump, a pneumatic pump, a hydraulic pump, a manual pump, etc.), oscillating membranes, a chemical reactor (e.g., a device that utilizes chemical reactions to generate flow), a user chargeable bladder or canister having a handheld bellows mechanism, chemical reactions, fans, pistons, or other electronic mechanisms, or any other device or system configured to generate flow of the fluid into the interior space 14'. In some embodiments, the fluid includes ambient air, oxygen, hydrogen, argon, helium, nitrogen, chlorofluorocarbon, hydroflouroalkanes, hydrofluoroolefin, any other suitable propellant, or combinations thereof. For example, in some embodiments the fluid includes ambient air enriched with some or all of the previously mentioned fluids in various mixtures.

In some embodiments, a flow regulator is associated with the fluid source 30 to manage the volume and/or speed of flow into the interior space 14'. The particular design and implementation of a flow regulator varies by embodiment. For example, a flow regulator is employed in some embodiments that utilize compressed gas as the external fluid source.

Figure 2:
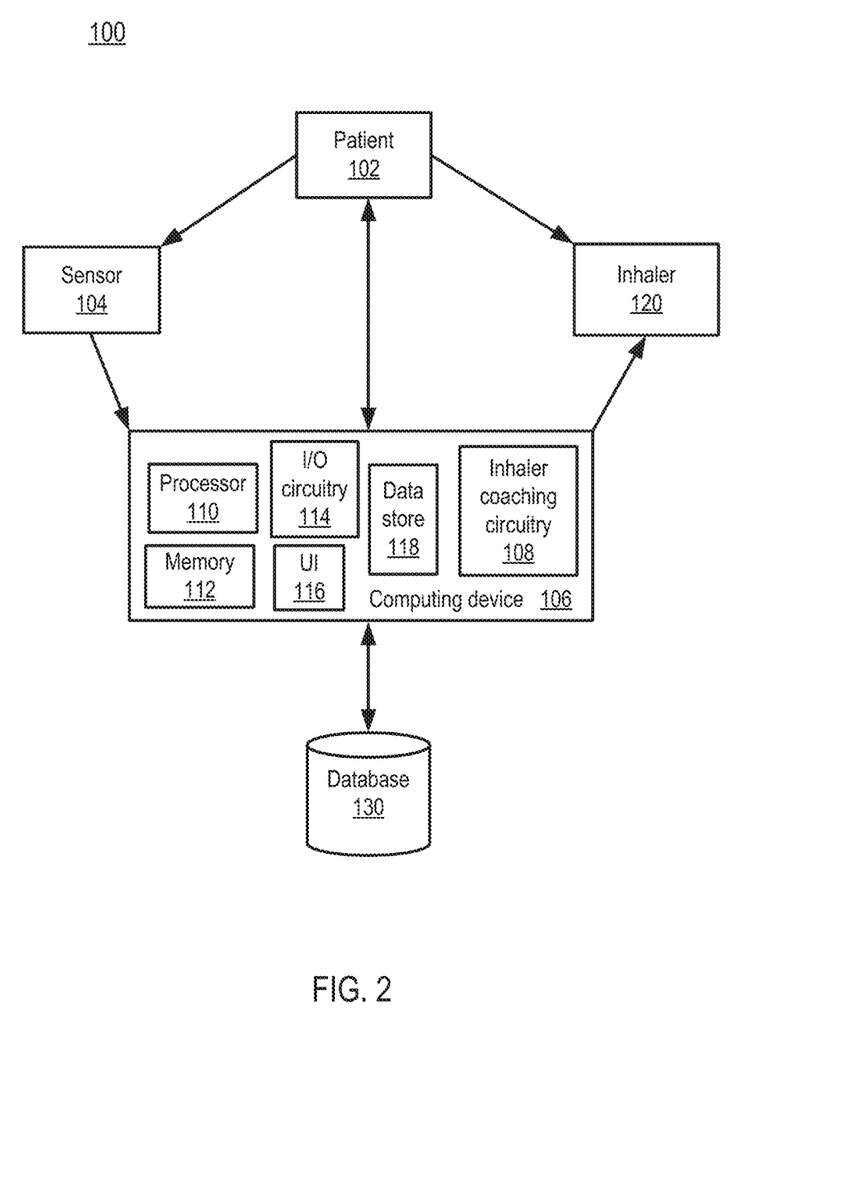
FIG. 2 is a functional block diagram of a system for coaching a patient to use an inhaler with a medication delivery assistance device for medication delivery according to some embodiments of the present technology.

FIG. 2 illustrates a functional block diagram of an inhaler coaching system 100 according to some embodiments of the present technology. Inhaler coaching system 100 works with a patient 102 (i.e., a user of device 10, 10') who has been prescribed a medication delivery via an inhaler 120 used with a medication delivery assistance device, such as device 10, 10' described above. A sensor 104 is configured to obtain respiratory behavior data of the patient 102 and to communicate the respiratory behavior data to a computing device 106. The sensor 104 may include invasive or non-invasive monitoring of the patient 102 via any combination of the types of sensors discussed in more detail below regarding medication delivery coaching method 200 of FIG. 3.

Computing device 106 may include, but is not limited to, a computing system (e.g., a server, a workstation computer, a desktop computer, a laptop computer, a tablet computer, an ultraportable computer, an ultramobile computer, a netbook computer and/or a subnotebook computer, etc.) and/or a Smartphone. Computing device 106 includes a processor 110, a memory 112, input/output ("I/O") circuitry 114, a user interface ("UI") 116, data store 118, and inhaler coaching circuitry 108.

Processor 110 is configured to control overall operations of the computing device 106 and its associated components, such as inhaler coaching circuitry 108 which includes the algorithms discussed in more detail below regarding medication delivery coaching method 200 of FIG. 3. Memory 112 may be configured to store data associated with inhaler coaching circuitry 108. I/O circuitry 114 may be configured to provide wired and/or wireless communication functionality for inhaler coaching circuitry 108. For example, I/O circuitry 114 may be configured to receive respiratory behavior data from the sensor 102, provide inhaler and external fluid source actuation cues to the patient 102 after processing and analysis of the respiratory behavior data by inhaler coaching circuitry 108, and receive user feedback from the patient 102. In another example, I/O circuitry 114 may be configured to receive inhaler characteristics data, historical user data (of the patient 102 and/or other similarly matched users), environmental initiative data, etc. from database 130, as discussed in more detail below regarding medication delivery coaching method 200 of FIG. 3. UI 116 may include a user input device (e.g., keyboard, mouse, microphone, touch sensitive display, etc.) and/or a user output device, e.g., a display. Data store 118 may be configured to store one or more of respiratory behavior data, inhaler requirement data, inhaler characteristics data, historical user data, environmental initiative data, etc.

Figure 3:
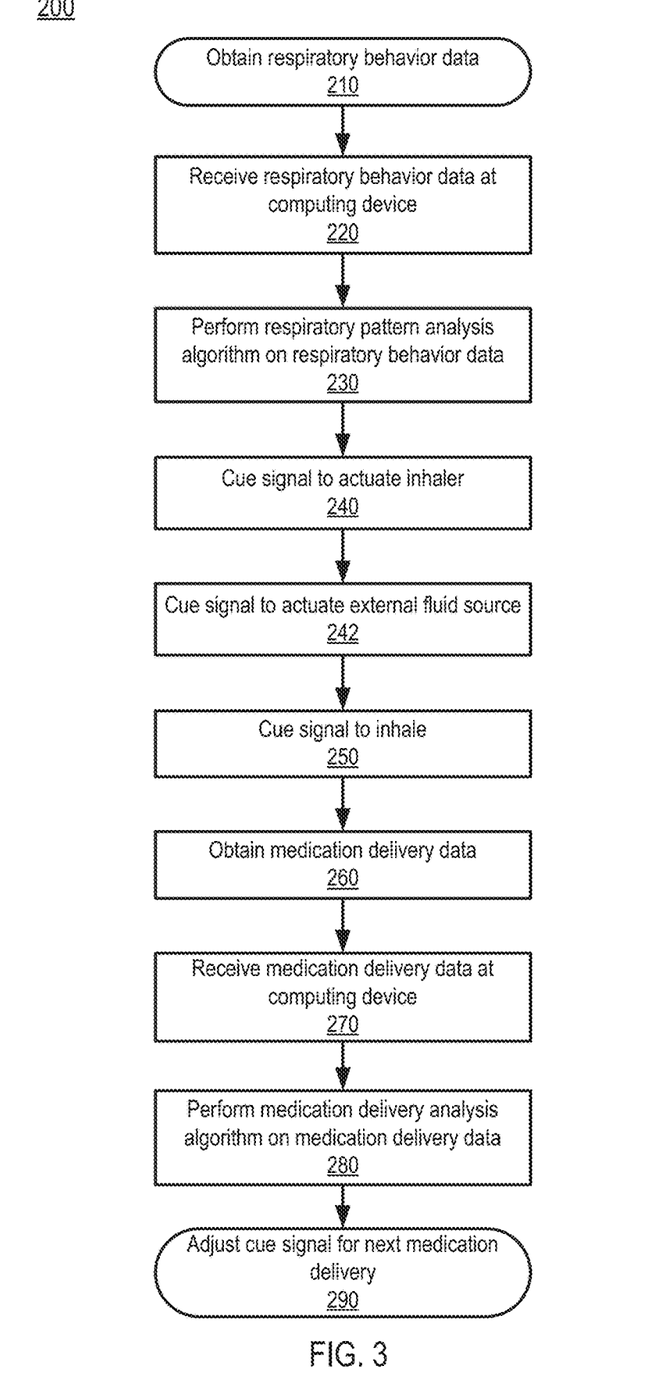
FIG. 3 is a flowchart of a method of coaching a patient to use an inhaler with a medication delivery assistance device for medication delivery according to some embodiments of the present technology.

FIG. 3 illustrates a flowchart of a medication delivery coaching method 200 according to some embodiments of the present technology. At 210, the method 200 includes obtaining, via the sensor 104, respiratory behavior data of the patient 102. The sensor includes any respiratory monitoring technology for measuring breathing that outputs an electronic signal indicative of one or more characteristics of a patient's breathing. In one embodiment, the sensor is a flow sensor that measures flow rate and volume. In other embodiments, the sensor includes invasive monitoring, non-invasive monitoring, skin monitoring, mouth and/or nose monitoring, cardiac activity monitoring, neural activity monitoring, etc., or combinations thereof. For example, in some embodiments, the sensor includes chest straps and bands that fit around the patient's chest or abdomen and measure the expansion and contraction during breathing. The chest straps and bands include digital or analog strain gauges to detect movement. The chest straps and bands can be wired or wireless. In some embodiments, the sensor includes wearable devices (e.g., Smartwatches, Fitness Trackers, etc.) that are configured to estimate respiration rates through motion detection, ballistocardiography, or photoplethysmography. In some embodiments, the sensor includes spirometers that measure the volume of air inspired and expired by the patient's lungs via pressure, flow, and/or oscillometry methods. In some embodiments, the sensor includes microphone-based systems wherein a microphone (e.g., a dedicated microphone, a microphone that is part of a Smartphone or Smart Speaker, etc.) is placed near the patient's mouth or nose to detect breath sounds. In some embodiments, the sensor includes thermal sensors placed under the patient's nose to detect the change in temperature between inhaled and exhaled air. In some embodiments, the sensor includes impedance pneumography to measure changes in electrical impedance between two electrodes places on the patient's chest to estimate respiratory activity. In some embodiments, the sensor includes capnography devices (e.g., portable or stationary) to measure the concentration of carbon dioxide in exhaled air to provide data on respiratory rate and depth. In some embodiments, the sensor includes camera-based monitoring wherein a camera (e.g., a dedicated camera, a camera that is part of a Smartphone, etc.) captures the patient's chest movements and uses image processing algorithms to calculate the respiratory rate. In some embodiments, the sensor includes radar-based or radio wave systems that use radar or radio waves to detect body movements associated with breathing. These systems may include standalone devices or be integrated into larger systems such as Smart Home Networks. In some embodiments, the sensor includes bioimpedance measurement methods that estimate lung volume by measuring the resistance of the patient's body to small amount of electric current. In some embodiments, the sensor includes any combination of the respiratory monitoring technologies discussed above.

At 220 the method 200 includes receiving, at the computing device 106, the respiratory behavior data obtained by the sensor. Inhaler coaching circuitry 108 of the computing device 106 is configured to execute the automated processes discussed herein to analyze the patient's breathing pattern, generate cues for training the patient how to correctly use the inhaler, monitor the patient's use of the inhaler after receiving the training cues, and adjusting the training cues based on how efficiently the patient uses the inhaler and the device. The processor 110 and inhaler coaching circuitry 108, and their associated components, enable the computing device 106 to perform a series of computer-readable instructions to execute the automated processes discussed herein.

At 230 the method 200 includes performing a respiratory pattern analysis algorithm on the respiratory behavior data to determine a desired interval of medication delivery. In some embodiments, the desired interval of medication delivery is in the range of about 0.5 seconds to about 1.5 seconds after the patient's inhalation phase begins. In some embodiments, the desired interval of medication delivery is about 1 second after the patient's inhalation phase begins. However, the present technology is not limited thereto and contemplates embodiments where the desired interval of medication delivery occurs at various time instances and intervals after the patient's inhalation phase begins, such as 0.5 seconds, 1.5 seconds, about 2 seconds, in the range of about 0.5 seconds to about 1 second, in the range of about 1 second to about 1.5 seconds, in the range of about 1 second to about 2 seconds, etc. As discussed in more detail below, after determining the desired interval of medication delivery, the software communicates a first cue signal to actuate the inhaler to deliver the medication into the interior space of the chamber housing, communicates a second cue signal to actuate the external fluid source to provide an external flow along the medication flow path having a desired flow rate, and communicates a third cue signal for the user to inhale to achieve the desired interval of medication delivery. Thus, the software automates medication introduction into the device that is synchronized with the user's respiratory cycle and automates actuation of the external fluid source that is also synchronized with the user's respiratory cycle at the appropriate time to achieve the desired interval of medication delivery. In some embodiments, the system monitors, via the sensor, the flow along the medication flow path within the chamber of the device before, during, and after each method step discussed herein. For example, the sensor initially monitors the patient's breathing pattern and the environment within the chamber, then the inhaler is actuated and the sensor monitors the device to ensure that the medication was delivered correctly into the chamber, then the external fluid source is actuated and the sensor monitors that the flow path along the medication flow path is within the desired flow rate range as discussed herein, then the patient inhales and the sensor monitors whether the desired interval of medication delivery was achieved. Although the cue signals are described as "first," "second," and "third," these descriptors are merely used to indicate that they are separate cue signals and are not intended to limit the method to any particular order. Thus, the present technology contemplates embodiments in which the cue signals occur in any order, such as the first, second, and third cues occurring in numerical order; first and second cue signals occurring synchronously; the third cue signal occurring before the first and/or second cue signal; the first and third cue signals occurring synchronously and the second cue signals occurring last; etc.

Figure 4:
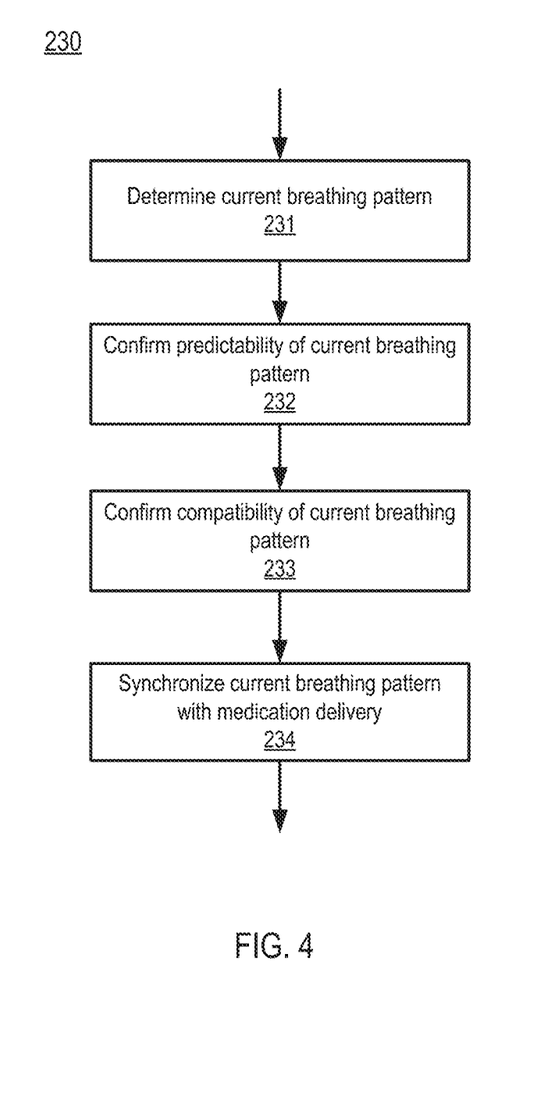
FIG. 4 is a flowchart further outlining the respiratory pattern analysis algorithm of the method of FIG. 3.

FIG. 4 illustrates a flowchart of the step 230 of performing the respiratory pattern analysis algorithm according to some embodiments of the present technology. At 231, the respiratory pattern analysis algorithm includes analyzing the respiratory behavior data to determine the current breathing pattern of the patient and to confirm that the current breathing pattern is predictable within a predetermined margin of error. In some embodiments, the respiratory pattern analysis algorithm determines the current breathing pattern by measuring the integral of flow over time (i.e., the mathematical integral of the volume of air measured by the sensor during inhalation and exhalation for a single breath) for three breaths and comparing the integral of flow across the three breaths. In some embodiments, if the integral of flow is within about 10% for each breath, then the current breathing pattern is confirmed as predictable. In some embodiments, the respiratory pattern analysis algorithm determines the current breathing pattern by measuring the total tidal volume for three breaths (i.e., the sensor measures the total volume of air inhaled and exhaled for each breath) and ensuring that there is about 10% or less error over the three breaths. However, the present technology is not limited in this regard and contemplates embodiments that measure the integral of flow and/or the total tidal volume over any number of breaths (e.g., 2, 4, 5, 6, etc.) and that use different predetermined margins of error (e.g., the integral of flow and/or the total tidal volume being within about 5%, 15%, in the range of about 5% to about 15%, etc., for each breath).

At 232, the respiratory pattern analysis algorithm confirms that the current breathing pattern is predictable within the predetermined margin of error by additional and/or alternative means. For example, in some embodiments, the respiratory pattern analysis algorithm includes signal processing algorithms that use filtering techniques such as Fourier transforms, wavelet transforms, or digital filtering. In some embodiments, the respiratory pattern analysis algorithm includes machine learning models that use advanced algorithms such as recurrent neural networks ("RNNs") or long short-term memory ("LSTM") networks to predict future respiratory patterns based on past data from the patient and, in some embodiments, a broader set of data from similarly matched users. In some embodiments, the respiratory pattern analysis algorithm includes statistical analysis techniques such as autocorrelation or spectral density estimation to measure the predictability of the patient's respiratory cycle and, in some embodiments, measure entropy (e.g., sample entropy, approximate entropy, cross entropy, multi-scale entropy). In some embodiments, the respiratory pattern analysis algorithm includes biofeedback training wherein visual, auditory, and/or haptic feedback is provided to guide the patient to regulate their breathing to generate predictable breathing pattern. In some embodiments, the respiratory pattern analysis algorithm includes anomaly detection algorithms that are configured to exclude abnormal breaths from the pattern recognition process. In some embodiments, the respiratory pattern analysis algorithm includes data normalization via integration with other physiological data such as heart rate or body temperature to enhance the predictability of the respiratory cycle through artificial intelligence ("AI") and methods of multivariate analyses. In some embodiments, the respiratory pattern analysis algorithm includes deep learning models such as convolutional neural networks ("CNNs") to recognize complex patterns in the patient's respiratory cycle. In some embodiments, the respiratory pattern analysis algorithm includes ensemble models that combine a plurality of prediction models that each predict different aspects of the patient's respiratory cycle to create a more robust and accurate overall prediction model. In some embodiments, the respiratory pattern analysis algorithm includes adaptive algorithms that adjust their behavior based on the patient's respiratory behavior data that they are processing. In some embodiments, the respiratory pattern analysis algorithm includes any combination of the breath pattern prediction methods discussed above.

At 233, the respiratory pattern analysis algorithm includes confirming that the current breathing pattern is compatible with medication delivery via actuation of the inhaler and the external fluid source. In some embodiments, the respiratory pattern analysis algorithm confirms the compatibility of the current breathing pattern by determining if the flow rate generated by the external fluid source is within a desired range. In some embodiments, the desired flow rate range is between about 15 L/min to about 90 L/min. In some embodiments, the desired flow rate range is between about 20 L/min to about 40 L/min. In some embodiments, the desired flow rate range is between about 25 L/min to about 35 L/min. However, the present technology is not limited to any particular number range for the desired flow rate as the algorithm is configured to augment the flow rate to be within a range that is sufficient to achieve the desired interval of medication delivery. For example, the system measures the patient's breathing pattern flow and the external flow generated by the external fluid source, determines if the overall flow rate is sufficient to achieve the desired interval of medication delivery, and augments the external flow generated by the external fluid source if the overall flow is insufficient. The flow rate of the current breathing pattern can be obtained directly from the respiratory behavior data measured by the sensor 104 or calculated by the respiratory pattern analysis algorithm from the respiratory behavior data. For example, in embodiments where the sensor 104 measures respiratory behavior data as a unit of pressure (e.g., psi, bar, etc.) and the respiratory pattern analysis algorithm calculates the flow rate therefrom.

In some embodiments, the system includes a medication delivery device database that is accessed by the respiratory pattern analysis algorithm. The medication delivery device database includes data on various inhaler types, various valved holding chamber types, and various spacer types, each with their specific requirements for desired medication delivery. These requirements can include inhalation speed, volume, flow rate, and breath-holding duration. The system is configured to match the patient's inhaler to its corresponding entry in the database to extract the inhaler's specific requirements.

In some embodiments, the respiratory pattern analysis algorithm includes respiratory pattern matching wherein the system cross-references the patient's established respiratory pattern with the inhaler's requirements to ensure that the patient's breath pattern, such as inhalation speed and volume, aligns with the inhaler's requirements for desired medication delivery and/or is similarly matched with the patient's prior breath patterns or breath patterns of other users that have had successful clinical outcomes with the same inhaler.

In some embodiments, the respiratory pattern analysis algorithm includes inhalation profile analysis wherein the system analyzes the patient's inhalation profile, including inhalation speed, volume, and depth, to ensure it is compatible with the inhaler's requirements. In some embodiments, if the patient's inhalation profile does not meet the inhaler's requirements, the system provides feedback and coaching to help the patient adjust their inhalation technique or recommend an alternative inhaler or therapeutic option. Different inhalers require different flow rates to deliver the API. In some embodiments, the respiratory pattern analysis algorithm is informed of what type of inhaler is being used by the patient and thus measures the flow rates generated by the patient in real-time to ensure that the flow rates are sufficient for the given type of medication. If the flow rates are sufficient, then the medication delivery proceeds as planned via the method steps discussed herein. If the flow rates are insufficient, then the system recommends appropriate augmentation of the external flow generated by the external fluid source. In some embodiments, if the flow rates are insufficient, then the system recommends a more appropriate type of delivery device to match the patient's needs and ability to generate flow rates.

In some embodiments, the respiratory pattern analysis algorithm includes flow rate monitoring wherein the system monitors the patient's flow rate during inhalation and compares it to the inhaler's requirements. If the patient's flow rate is too low or too high, the system provides feedback and coaching to help the patient adjust their inhalation technique. For example, in some embodiments the respiratory pattern analysis algorithm determines if the flow rate is in the range of about 20 L/min to about 90 L/min and instructs the system to augment the external flow generated by the external fluid source and/or provide feedback and coaching to the patient if the flow rate is outside this range.

In some embodiments, the respiratory pattern analysis algorithm includes adaptive algorithms that are configured to adjust the timing of inhaler cues based on the patient's changing respiratory patterns. If the patient's breathing becomes irregular or if the inhalation profile does not meet the inhaler's requirements, the system is configured to delay or modify the cues until the patient's breathing stabilizes.

In some embodiments, the respiratory pattern analysis algorithm includes sensor fusion wherein the system includes additional sensors, such as flow sensors or pressure sensors, to provide a more comprehensive view of the patient's breath pattern. By combining data from multiple sensors, the system is configured to more accurately assess whether the patient's breath pattern is sufficient for medication delivery.

In some embodiments, the respiratory pattern analysis algorithm includes user feedback wherein the system permits the patient to provide feedback on the effectiveness of the medication delivery. The respiratory pattern analysis algorithm is configured to use this feedback to improve its accuracy in assessing the sufficiency of the respiratory pattern. For example, if the patient rates their perceived efficacy, the system can then aim to adjust itself to achieve a higher patient score based on a predetermined targeted end point.

In some embodiments, the respiratory pattern analysis algorithm includes clinical outcome monitoring wherein the system monitors (via e.g., the various sensors discussed herein, user feedback, etc.) clinical outcomes, such as symptom relief or lung function improvements, to assess the effectiveness of the medication delivery. If the patient does not experience the expected benefits, the system is configured to adjust the respiratory pattern analysis algorithm or recommend a different inhaler type, a different valved holding chamber type, a different space type, a different flow rate generated by the external fluid source, or a different external fluid source type.

In some embodiments, the respiratory pattern analysis algorithm includes AI-enhanced prediction models that are configured to predict the patient's future breath patterns based on historical data. In some embodiments, the respiratory pattern analysis algorithm includes data augmentation techniques that are configured to generate synthetic respiratory patterns based on the patient's actual respiratory pattern data. In some embodiments, the respiratory pattern analysis algorithm includes any combination of the breath pattern compatibility confirmation methods discussed above.

At 234, the respiratory pattern analysis algorithm includes synchronizing the current breath pattern with the actuation of the external fluid source to determine the desired interval of medication delivery. The respiratory pattern analysis algorithm is configured to synchronize the patient's current tidal breath inspiration with the medication delivery such that the patient can precisely time actuation of the external fluid source to receive an effective dose of the medication. For example, in some embodiments, the respiratory pattern analysis algorithm includes inhalation phase detection to identify the onset of the inhalation phase of the patient's respiratory cycle and then electronically cue the patient (or send an electronic actuation signal to an actuation mechanism of the external fluid source) to trigger the external fluid source to actuate at the start of this phase. In some embodiments, the respiratory pattern analysis algorithm cues for external fluid source actuation synchronously with the start of the inhalation phase. In some embodiments, the respiratory pattern analysis algorithm cues for external fluid source actuation about 1 second after the inhalation phase begins. In some embodiments, the respiratory pattern analysis algorithm cues for external fluid source actuation in the range of about 0.5 seconds to about 1.5 seconds after the inhalation phase begins. However, the present technology is not limited thereto and contemplates embodiments where the respiratory pattern analysis algorithm cues for external fluid source actuation at different times after the inhalation phase begins, such as 0.5 seconds, 1.5 seconds, about 2 seconds, in the range of about 0.5 seconds to about 1 second, in the range of about 1 second to about 1.5 seconds, in the range of about 1 second to about 2 seconds, etc.

In some embodiments, the respiratory pattern analysis algorithm includes desired flow rate identification that is configured to analyze the patient's inhalation flow rate and determine the desired interval for external fluid source actuation. The algorithm monitors the patient's flow rate in real-time and cues the patient or an actuation mechanism of the external fluid source (e.g., remove a barrier to flow, close a bypass door, etc.) to actuate when the flow rate reaches the desired value. In some embodiments, the desired value is determined by the algorithm measuring the duration of inhalation and determining the point of greatest flow of inhalation, at which point actuation of the external fluid source is triggered (e.g., by cueing the patient or automatically by signaling the actuation mechanism of the external fluid source).

In some embodiments, the respiratory pattern analysis algorithm includes volume-based actuation that is configured to monitor the patient's inhalation volume and trigger the external fluid source when a specific volume threshold (e.g., determined via the inhaler's specific requirements) is reached. In some embodiments, the respiratory pattern analysis algorithm includes inhalation patterns wherein the algorithm analyzes historical data (e.g., the patient's past respiratory pattern data) to predict the timing and characteristics of the patient's next inhalation and actuates the inhaler at the desired interval (e.g., determined via the inhaler's specific requirements).

In some embodiments, the respiratory pattern analysis algorithm includes AI-enhanced prediction models, such as RNNs and LSTM networks, to predict the patient's inhalation patterns. In some embodiments, the respiratory pattern analysis algorithm includes user preferences wherein the patient is permitted to customize the timing of inhaler and/or external fluid source actuation based on their preferences. For example, the patient may customize the timing of inhaler and/or external fluid source actuation to occur automatically 1 second before or 1 second after their inhalation phase begins. In some embodiments, the respiratory pattern analysis algorithm includes any combination of the current breath pattern synchronization methods discussed above.

In some embodiments, the method 200 includes evaluating a pseudo actuation of the inhaler and/or external fluid source by the patient. The system communicates a sample cue signal to the patient to perform a pseudo actuation of the inhaler and/or external fluid source. Sample inhalation data of the patient is obtained by the sensor as the patient performs the pseudo actuation. The sample inhalation data is received at the computing device. The system performs the respiratory pattern analysis algorithm described above on the sample inhalation data. For example, in some embodiments the system cues the patient to perform a sample inhalation on the inhaler and/or external fluid source as if they intended to inhale while actuating the inhaler and/or external fluid source. As the patient performs the sample inhalation, the system receives sample inhalation data from the sensor and instructs the above-described algorithms to perform any combination of the above-described analyses as if the patient were actuating their inhaler and/or external fluid source, thereby performing a quality control step.

The sample inhalation provides additional benefits such as training and coaching, calibration, and personalization. Regarding training and coaching, a sample inhalation allows the patient to practice their inhalation technique under the guidance of the system. The system can provide real-time feedback on the patient's inhalation technique, such as inhalation speed, volume, and depth. This training can help the patient improve their technique and better ensure improved medication delivery during the actual inhalation. Regarding calibration, a sample inhalation can be used to calibrate the system's algorithms. By analyzing the patient's inhalation patterns during the sample inhalation, the system can adjust its algorithms to predict the patient's future inhalation patterns more accurately. In some embodiments, the system includes a calibration device to ensure that the sensor continuously functions as desired. Regarding personalization, a sample inhalation allows the system to personalize its algorithms to the patient's unique breathing patterns. During the sample inhalation, the system can determine whether the patient's breathing technique meets the inhaler's requirements for desired medication delivery. If the patient's breathing technique does not meet the inhaler's requirements, the system can provide feedback and coaching to help the patient adjust their breathing technique, augment the flow generated by the external fluid source, or recommend a different inhaler and/or external fluid source type.

At 240, the method 200 includes communicating a first cue signal to actuate the inhaler to deliver the medication into the interior space of the chamber housing. In some embodiments, the cue signal is communicated directly to the patient and/or the patient's healthcare provider and the cue signal includes an audio cue, a visual due, a haptic cue, etc., or combinations thereof. For example, in some embodiments, the cue is visual via activating a green light on the computing device that signals the patient to actuate the inhaler. In other embodiments, the cue signal is electronically communicated (e.g., via wires or wireless communication protocols) to an actuation mechanism of the inhaler to automatically actuate the inhaler. For example, in some embodiments the actuation mechanism includes a pressing device secured to the body of the inhaler and is configured to depress a pressurized cannister inside the inhaler to actuate medication delivery. The pressing device can be driven by any mechanical pressing means used in the art, such as a servo motor, hydraulic pump, pneumatic pump, etc. The actuation mechanism includes a microcontroller configured to receive the cue signal wirelessly (via e.g., Bluetooth, Wi-Fi, etc.) and activate the pressing device. In some embodiments, the computing device is integrally formed with the inhaler for directly communicating the cue signal to the actuation mechanism.

At 242, the method 200 includes communicating a second cue signal to actuate the external fluid source to deliver the fluid into the interior space and accelerate the movement of the medication along the medication flow path. In some embodiments, the second cue signal is communicated directly to the patient and/or the patient's healthcare provider and the cue signal includes an audio cue, a visual due, a haptic cue, etc., or combinations thereof. For example, in some embodiments, the cue is visual via activating a green light on the computing device that signals the patient to actuate the external fluid source. In other embodiments, the cue signal is electronically communicated (e.g., via wires or wireless communication protocols) to an actuation mechanism of the external fluid source to automatically actuate the external fluid source.

At 250, the method 200 includes communicating a third cue signal to the patient to inhale to achieve the desired interval of medication delivery. In some embodiments, the third cue signal includes an audio cue, a visual due, a haptic cue, etc., or combinations thereof. In some embodiments, the third cue is communicating synchronously with the second cue such that the patient inhales as the external fluid source is actuated. In some embodiments, the third cue is communicated at a predetermined interval (as determined by the respiratory pattern analysis algorithm discussed above) after the external fluid source is actuated to achieve the desired interval of medication delivery. In some embodiments, the third cue is communicated at a predetermined interval (as determined by the respiratory pattern analysis algorithm discussed above) before the external fluid source is actuated to achieve the desired interval of medication delivery. In some embodiments, the third cue is communicated at a predetermined interval (as determined by the respiratory pattern analysis algorithm discussed above) before either the inhaler or the external fluid source are actuated. In some embodiments, the third cue is communicated synchronously with the external fluid source and/or the inhaler actuation.

At 260, the method 200 includes obtaining medication delivery data based on the patient's inhalation. In some embodiments, the medication delivery data is obtained via the sensor discussed above. In some embodiments, the medication delivery data is obtained via an additional sensor, which may be any one or any combination of the types of sensors discussed above. At 270, the computing device receives the medication delivery data and, at 280, performs a medication delivery analysis algorithm on the medication delivery data to determine whether the patient achieved the desired interval of medication delivery. At 290, the method 200 includes adjusting at least one of the first, second, and third cue signals to achieve the desired interval for a future medication delivery. For example, if the patient received a visual cue and failed to achieve the desired interval, then the system can adjust the cue for the next medication delivery to include an audio cue. By way of another example, if the desired interval was not achieved because the flow rate was outside the desired flow rate range as discussed above, then the system can augment the flow generated by the external fluid source by adjusting the second cue signal to increase or decrease the flow rate provided by the external fluid source. By way of yet another example, if the desired interval was not achieved due to actuation and/or inhalation timing, then the system can adjust the first, second, and/or third cur signals to augment the timings of the inhaler actuation, the external fluid source actuation, and the patient's inhalation.

Figure 5:
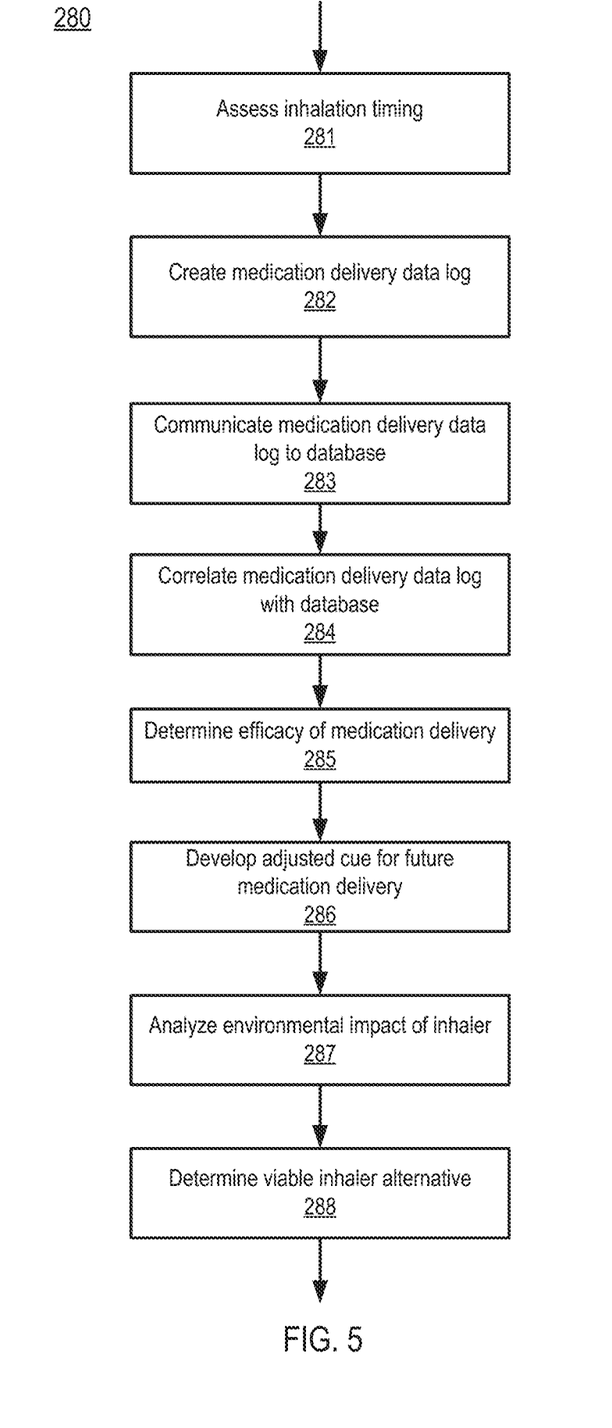
FIG. 5 is a flowchart further outlining the medication delivery analysis algorithm of the method of FIG. 3.

FIG. 5 illustrates a flowchart of the step 280 of performing the medication delivery analysis algorithm according to some embodiments of the present technology. In some embodiments, the medication delivery analysis algorithm is configured for monitoring and providing feedback regarding the efficacy of the medication delivery. At 281, the medication delivery analysis algorithm determines if the patient inhaled at the desired interval by assessing the inhalation timing. The medication delivery analysis algorithm is configured to confirm that medication delivery occurred at the appropriate time (i.e., whether the desired interval was achieved). At 282, the medication delivery analysis algorithm is configured to create an medication delivery instance data log of the medication delivery data and the timing information. At 283, the medication delivery instance data log is communicated to a storage, such as database 130. The medication delivery data log can be stored on the computing device and/or communicated to a remote computing device for local and/or remote storage and monitoring. For example, in some embodiments the medication delivery analysis algorithm confirms that medication delivery occurred at the appropriate time by monitoring, via the sensor, the medication flow path within the chamber of the device for the desired flow rate, as discussed above, during the patient's inhalation, which the algorithm records as an instance of medication delivery.

At 284, the medication delivery analysis algorithm is configured to correlate the medication delivery instance data log with additional data stored on the database, such as historical data of the patient, historical data of similarly diagnosed patients using the same type of inhaler as the patient, etc. The medication delivery analysis algorithm correlates the medication delivery instance data log with the additional data to track and monitor symptoms, side-effects, and/or exacerbations of the patient's underlying pathological condition that is being treated by the inhaler-delivered medication. For example, in some embodiments, the medication delivery analysis algorithm is configured for correlation and tracking regarding the patient's symptoms and any exacerbation of the symptoms. In some embodiments, the medication delivery analysis algorithm is configured to monitor the patient for side effects, such as coughing, or potential ineffective medication delivery, such as the patient failing to correctly actuate the inhaler and/or the external fluid source or failing to inhale at the appropriate time. In some embodiments, the medication delivery analysis algorithm is configured to compare the patient's records with other patients' records and propose alternative therapies that may be better tolerated by the patient and/or result in more effective medication delivery.

At 285, the medication delivery analysis algorithm is configured to determine the efficacy of the medication delivery. In some embodiments, the efficacy of the medication delivery is determined by analyzing the medication delivery data and assessing if the amount or percentage of the medication dose effectively received by the patient meets a predetermined threshold (also referred to herein as a success threshold). For example, in some embodiments the algorithm considers a successful medication delivery to mean that at least 95% of the medication dose was effectively received by the patient. In some embodiments, the algorithm considers a successful medication delivery to mean that at least 90% of the medication dose was effectively received by the patient. At 286, if the medication delivery analysis algorithm determined that the medication delivery was ineffective (i.e., the dose received by the patient was below the success threshold), the medication delivery analysis algorithm develops an adjusted third cue signal for the next medication delivery, as described above. In some embodiments, if the medication delivery analysis algorithm determined that the medication delivery was ineffective, the algorithm develops an adjusted second cue signal for the next medication delivery to more appropriately augment the external flow generated by the external fluid source.

In some embodiments, the medication delivery analysis algorithm includes continuous respiratory monitoring wherein the system is configured to continuously monitor the patient's respiratory patterns using the sensor to track metrics such as flow rate generated by the external fluid source, inhalation speed, volume, and depth, and the frequency and regularity of breaths. By such continuous monitoring, the system assesses the effectiveness of the medication delivery and identifies any changes in the patient's respiratory patterns.

In some embodiments, the medication delivery analysis algorithm includes medication adherence tracking wherein the system is configured to track the patient's medication adherence by recording the timing and frequency of medication delivery instances. The algorithm compares the patient's actual medication usage with the prescribed regimen and calculates adherence metrics, such as the percentage of doses taken on time, times when the patient does not use the medication correctly, and when the patient appears to be using the medication extra times which may suggest poor disease control.

In some embodiments, the medication delivery analysis algorithm includes user feedback wherein the system permits the patient to provide feedback on the effectiveness of the medication, any side effects experienced, and their overall satisfaction with the therapeutic regimen using the inhaler 120 with the device 10, 10' and external fluid source 30. In some embodiments, the medication delivery analysis algorithm includes clinical outcome monitoring wherein the system is configured to monitor clinical outcomes, such as symptom relief and/or improvement, pulmonary function changes, and quality of life measures. The algorithm tracks (e.g., by storing data in a database for future use and cross-reference with other data) data regarding patient responses to questionaries, patient-reported outcome measures, and objective tests such as spirometry or peak flow measurements.

In some embodiments, the medication delivery analysis algorithm includes alerts and notifications wherein the system is configured to generate alerts and notifications based on the patient's respiratory patterns, medication adherence, and clinical outcomes. These alerts may be sent to the patient, healthcare providers, or caregivers, depending on the patient's preferences. In some embodiments, the alerts provide recommendations for actions to take, such as adjusting the medication dosage, adding additional controller medications (e.g., allergy medicine, nasal sprays, oral medications such as antibiotics) or seeking medical attention. In some embodiments, the medication delivery analysis algorithm includes reports and dashboards wherein the system is configured to provide reports and dashboards that summarize the patient's respiratory patterns, medication adherence, and clinical outcomes. These reports may be accessible to the patient, healthcare providers, and caregivers, and provide a comprehensive view of the patient's respiratory health and treatment progress. In some embodiments, the above alerts, notifications, reports, and dashboards are provided to the patient via a display of the computing device or communicated to the patient's personal computing device such as a Smartphone. In some embodiments, the above alerts, notifications, reports, and dashboards are provided to healthcare providers and/or caregivers via a display of the computing device or communicated via a network to a remote server or computing device.

In some embodiments, the medication delivery analysis algorithm includes data sharing wherein the system permits the patient to share their data (e.g., via network communication to a remote server or computing device) with healthcare providers, caregivers, researchers, or other stakeholders. This data sharing facilitates collaboration and coordination among the patient's care team and supports evidence-based decision-making. In some embodiments, the medication delivery analysis algorithm includes telemedicine integration wherein the system is configured to integrate with telemedicine platforms (e.g., via wired or wireless network connections), permitting the patient to have virtual consultations with their healthcare providers. During such consultations, the healthcare provider may review the patient's respiratory patterns, medication adherence, and clinical outcomes, and adjust the treatment plan as needed.

In some embodiments, at 287, the medication delivery analysis algorithm includes environmental initiatives wherein the system is configured to access a database containing data regarding the environmental impact of all available inhalers. The algorithm cross-references data on the environmental impact of the patient's current inhaler with the environmental impact data of other available inhalers and, at 288, determines if a more environmentally friendly inhaler is available for use that still meets the patient's treatment regimen. If so, the algorithm recommends the patient switch to a different inhaler type. For example, the algorithm can recommend an inhaler that minimizes or avoids use of a propellant that is considered a greenhouse gas or is otherwise damaging. In some embodiments, the algorithm matches inhaler type for the patient based on which propellant is most clinically beneficial for the patient and recommends appropriate inhalers that use the beneficial propellant.

In some embodiments, the coaching software includes correct technique coaching instructions for the patient to follow when using an inhaler, such as a pMDI, with a valved holding chamber or spacer as described herein, including but not limited to: 1) Sit or stand up straight with the chin up and the neck slightly extended; 2) Shake the pMDI five times and remove its cap; 3) If using a valved spacer, shake it to check that the valve(s) is/are not stuck; 4) Hold the pMDI upright (with the canister up) and fit it into the spacer/VHC, hold the pMDI-spacer/VHC assembly horizontal, with one hand holding the pMDI between the index finger and thumb, and the other hand supporting the mouthpiece end of the spacer/VHC; 5) Breathe out as far as is comfortable; 6) Place the spacer/VHC mouthpiece between the teeth and seal the lips around it (or place the mask gently but tightly over the nose and lips); 7) Breathe in slowly, immediately press the inhaler once and continue to breathe in slowly (over 4-5 s) until the lungs are full; 8) Hold the breath for about 10 s or for as long as is comfortable, while breath holding, take the spacer/VHC out of the mouth (or lower the mask) and relax; 9) When further doses are required, repeat the above steps for each additional dose, including shaking the pMDI if necessary, multiple doses should not be fired together into the spacer/VHC and be inhaled with a single breath; and 10) When the session is ended, take the pMDI out of the spacer/VHC port, place the cap back on the pMDI, and rinse the mouth and gargle after inhalation of a corticosteroid.

In some embodiments, the coaching software includes inhaler and device maintenance instructions for the patient to follow, including but not limited to: 1) Disassemble the spacer/VHC after the last dose of the day; 2) Immerse the parts in lukewarm tap water containing a few drops of household detergent; 3) Shake the parts in the water and rub them with a soft cloth; 4) Leave the parts soaking for about 15 min, then take them out of the water; 5) Do not rinse or dry rub the inside of the parts; 6) Rinse soapy water off the mouthpiece; 7) Place the parts on a clean towel to air-dry overnight; 8) Reassemble the parts the next morning and check that the valve is not stuck; and 9) Wash the spacer/VHC every week.

Accordingly, embodiments of the present technology are configured to monitor and predict a patient's respiratory cycle to optimize medication delivery, whereas prior art inhaler coaching techniques and devices are limited to training the patient to inhale at the correct speed. Embodiments of the present technology are configured for use with any type of inhaler, whereas prior art inhaler coaching techniques and devices are specifically designed for use with pressurized metered dose inhalers ("pMDIs"). Embodiments of the present technology are configured to be implemented in a software application of any type of computing device that uses sensors to monitor the patient's breathing, whereas prior art inhaler coaching techniques and devices are limited to implementation as physical inhaler devices. Additionally, prior art inhaler coaching techniques and devices fail because they require the patient and/or healthcare provider to perform actions beyond the capability of the human mind, such as the ability to accurately and precisely detect breath patterns, control breath speed and timing, synchronize actuation cues with the breath patterns, monitor and analyze medication dose results, etc. Thus, the present technology improves computer functionality and respiratory medication delivery.

Some embodiments of the present technology assist patients in avoiding common inhaler use errors, spacer use errors, and valved holding chamber use errors such as: perceiving the reduction in the deposition of large particles in the oropharynx as a reduction in drug delivery, incorrect inhaler preparation, failure to remove protective cap, proper body posture, proper inhaler positioning during preparation and inhalation, exhalation completely before inhalation, failure to seal teeth and lips around mouthpiece, not having an empty mouth before inhalation, actuation of the inhaler at incorrect time relative to breathing in, failing to hold breath for sufficient time, not breathing out calmly after inhalation, and not rinsing mouth. Many of these errors are addressed by prompts from the system to the user.

As will be appreciated by those of skill in the art, embodiments of the present technology can improve health outcomes, some of which can be measured with the clinical COPD Questionnaire ("CCQ"), the COPD Assessment Test ("CAT"), or the St. George's Respiratory Questionnaire ("SGRQ").

As will be apparent to those skilled in the art, various modifications, adaptations, and variations of the foregoing specific disclosure can be made without departing from the scope of the technology claimed herein. The various features and elements of the technology described herein may be combined in a manner different than the specific examples described or claimed herein without departing from the scope of the technology. In other words, any element or feature may be combined with any other element or feature in different embodiments, unless there is an obvious or inherent incompatibility between the two, or it is specifically excluded.

References in the specification to "one embodiment," "an embodiment," etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described.

The singular forms "a," "an," and "the" include plural reference unless the context clearly dictates otherwise. Thus, for example, a reference to "a plant" includes a plurality of such plants. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition, or step being referred to is an optional (not required) feature of the technology.

The term "and/or" means any one of the items, any combination of the items, or all of the items with which this term is associated. The phrase "one or more" is readily understood by one of skill in the art, particularly when read in context of its usage.

Each numerical or measured value in this specification is modified by the term "about." The term "about" can refer to a variation of +5%, +10%, +20%, or +25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents of carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third, and upper third, etc.

As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the technology encompasses not only the entire group listed as a whole, but each member of the group individually and all possible subgroups of the main group. Additionally, for all purposes, the technology encompasses not only the main group, but also the main group absent one or more of the group members. The technology therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

What is claimed is:

1. A medication delivery assistance device comprising:
a chamber housing defining an interior space;
a first input port at a first end of the chamber housing, the first input port configured to receive a portion of an inhaler configured to deliver medication into the interior space;
an output port at a second end of the chamber housing, the output port having a user interface configured to define a medication flow path from the first input port through the interior space and out the output port;
a second input port in the chamber housing, the second input port configured to receive at least a portion of an external fluid source configured to deliver a fluid into the interior space to accelerate movement of the medication along the medication flow path;
a sensor configured to obtain respiratory behavior data of a user of the system; and
input/output circuitry configured to:
transmit the respiratory behavior data to a computing device comprising inhaler coaching circuitry;
receive a first cue signal from the computing device to actuate the inhaler to deliver the medication into the interior space of the chamber housing;
receive a second cue signal from the computing device to actuate the external fluid source; and
receive a third cue signal from the computing device to communicate to the user to inhale to achieve the desired interval of medication delivery.

2. The medication delivery assistance device of claim 1, wherein the output port comprises a valve in the user interface, the valve is moveable between a closed position and an open position such that the output port defines the medication flow path when the valve is in the open position.

3. The medication delivery assistance device of claim 1, wherein the external fluid source is a fan, a compressed tank, a pump, oscillating membranes, a chemical reactor, a user chargeable bladder or canister having a handheld or electronic bellows mechanism, or combinations thereof.

4. The medication delivery assistance device of claim 1, wherein the fluid comprises ambient air, oxygen, hydrogen, argon, helium, nitrogen, chlorofluorocarbon, hydroflouroalkanes, hydrofluoroolefin, or combinations thereof.

5. An individualized medication delivery system comprising:
a medication delivery assistance device comprising a chamber housing defining an interior space, a first input port at a first end of the chamber housing, a second input port in the chamber housing, and an output port at a second end of the chamber housing, the output port having a user interface configured to define a medication flow path from the first input port through the interior space and out the output port;
an inhaler partially received in the first input port and configured to deliver medication into the interior space of the chamber housing;
an external fluid source at least partially received in the second input port and configured to deliver a fluid into the interior space to accelerate movement of the medication along the medication flow path;
a sensor configured to obtain respiratory behavior data of a user of the system; and
a computing device configured to receive the respiratory behavior data, the computing device comprising inhaler coaching circuitry and a memory configured to execute instructions of the inhaler coaching circuitry via at least one processor, the instructions comprising:
obtaining, via the sensor, respiratory behavior data of the user;
receiving, at the computing device, the respiratory behavior data;
performing a respiratory pattern analysis algorithm on the respiratory behavior data to determine a desired interval of medication delivery;
communicating a first cue signal to actuate the inhaler to deliver the medication into the interior space of the chamber housing;
communicating a second cue signal to actuate the external fluid source; and
communicating a third cue signal to the user to inhale to achieve the desired interval of medication delivery.

6. The system of claim 5, wherein the instructions further comprise:
obtaining, via the sensor, medication delivery data based on the user's inhalation in response to the third cue signal;

receiving, at the computing device, the medication delivery data;

performing a medication delivery analysis algorithm on the medication delivery data to assess the efficacy of the medication delivery; and adjusting, if the efficacy of the medication delivery is below a predetermined threshold, at least one of the first, second, and third cue signals to improve the efficacy of a future medication delivery.

7. The system of claim 6, wherein performing the medication delivery analysis algorithm comprises:

determining if the user inhaled at the desired interval;

creating medication delivery instance data log based, at least in part, on the medication delivery data;

communicating the medication delivery instance data log to a database;

correlating the medication delivery instance data log with historical data of the user and historical data of similarly diagnosed third party users stored on the database to track and monitor symptoms, side-effects, and exacerbations of a pathological condition of the user being treated by the medication;

determining the efficacy of the medication delivery based, at least in part, on the correlated medication delivery instance data log; and developing an adjusted cue signal to improve the efficacy of a future medication delivery.

8. The system of claim 5, wherein the first and second cue signals are communicated to the user and/or the user's healthcare provider, and the first, second, and third cue signals each comprise an audio cue, a visual cue, a haptic cue, or combinations thereof.

9. The system of claim 5, wherein the output port comprises a valve in the user interface, the valve is moveable between a closed position and an open position such that the output port defines the medication flow path when the valve is in the open position.

10. The system of claim 5, wherein the external fluid source is a fan, a compressed tank, a pump, oscillating membranes, a chemical reactor, a user chargeable bladder or canister having a handheld or electronic bellows mechanism, or combinations thereof.

11. The system of claim 5, wherein the fluid comprises ambient air, oxygen, hydrogen, argon, helium, nitrogen, chlorofluorocarbon, hydroflouroalkanes, hydrofluoroolefin, or combinations thereof.

12. The system of claim 5, wherein performing the respiratory pattern analysis algorithm comprises:

analyzing the respiratory behavior data to determine a current breathing pattern of the user;

confirming that the current breathing pattern is predictable within a predetermined margin of error;

confirming that the current breathing pattern is compatible with medication delivery via the inhaler and the valved holding chamber; and synchronizing the current breathing pattern with the actuation of the external fluid source to determine the desired interval of medication delivery.

13. A method of coaching a user on medication delivery via an inhaler and a medication delivery assistance device, the method comprising:

providing a medication delivery assistance device comprising a chamber housing defining an interior space, a first input port at a first end of the chamber housing, a second input port in the chamber housing, and an output port at a second end of the chamber housing, the output port having a user interface configured to define a medication flow path from the first input port through the interior space and out the output port;

providing an inhaler partially received in the first input port and configured to deliver medication into the interior space of the chamber housing;

providing an external fluid source at least partially received in the second input port and configured to deliver a fluid into the interior space to accelerate movement of the medication along the medication flow path;

obtaining, via a sensor, respiratory behavior data of the user;

receiving, at a computing device, the respiratory behavior data;

performing a respiratory pattern analysis algorithm on the respiratory behavior data to determine a desired interval of medication delivery;

communicating a first cue signal to actuate the inhaler to deliver the medication into the interior space of the chamber housing;

communicating a second cue signal to actuate the external fluid source; and communicating a third cue signal to the user to inhale to achieve the desired interval of medication delivery.

14. The method of claim 13, wherein performing the respiratory pattern analysis algorithm comprises:

analyzing the respiratory behavior data to determine a current breathing pattern of the user;

confirming that the current breathing pattern is predictable within a predetermined margin of error;

confirming that the current breathing pattern is compatible with medication delivery via the inhaler and the valved holding chamber; and synchronizing the current breathing pattern with the actuation of the external fluid source to determine the desired interval of medication delivery.

15. The method of claim 13, further comprising:

obtaining, via the sensor, medication delivery data based on the user's inhalation in response to the third cue signal;

receiving, at the computing device, the medication delivery data;

performing a medication delivery analysis algorithm on the medication delivery data to assess the efficacy of the medication delivery; and adjusting, if the efficacy of the medication delivery is below a predetermined threshold, at least one of the first, second, and third cue signals to improve the efficacy of a future medication delivery.

16. The method of claim 15, wherein performing the medication delivery analysis algorithm comprises:

determining if the user inhaled at the desired interval;

creating medication delivery instance data log based, at least in part, on the medication delivery data;

communicating the medication delivery instance data log to a database;

correlating the medication delivery instance data log with historical data of the user and historical data of similarly diagnosed third party users stored on the database to track and monitor symptoms, side-effects, and exacerbations of a pathological condition of the user being treated by the medication;

determining the efficacy of the medication delivery based, at least in part, on the correlated medication delivery instance data log; and developing an adjusted cue signal to improve the efficacy of a future medication delivery.

17. The method of claim 13, wherein the first and second cue signals are communicated to the user and/or the user's healthcare provider, and the first, second, and third cue signals each comprise an audio cue, a visual cue, a haptic cue, or combinations thereof.

18. The method of claim 13, wherein the output port comprises a valve in the user interface, the valve is moveable between a closed position and an open position such that the output port defines the medication flow path when the valve is in the open position.

19. The method of claim 13, wherein the external fluid source is a fan, a compressed tank, a pump, oscillating membranes, a chemical reactor, a user chargeable bladder or canister having a handheld or electronic bellows mechanism, or combinations thereof.

20. The method of claim 13, wherein the fluid comprises ambient air, oxygen, hydrogen, argon, helium, nitrogen, chlorofluorocarbon, hydroflouroalkanes, hydrofluoroolefin, or combinations thereof.

* * * * *